United States Patent
Crepeau et al.

(12) 
(10) Patent No.: US 6,391,326 B1
(45) Date of Patent: May 21, 2002

(54) STABLE EMULSIONS, PREPARATION METHODS AND APPLICATIONS

(75) Inventors: Colette Crepeau, Nogent sur Oise; Pierre Hoerner, Horbourg-Wihr; Gérard Riess, Mulhouse, all of (FR)

(73) Assignee: Hutchinson, Paris (FR)

( * ) Notice: Subject to any disclaimer, the term of this patent is extended or adjusted under 35 U.S.C. 154(b) by 0 days.

(21) Appl. No.: 09/423,638

(22) PCT Filed: Mar. 16, 1999

(86) PCT No.: PCT/FR99/00586

§ 371 Date: Feb. 7, 2000

§ 102(e) Date: Feb. 7, 2000

(87) PCT Pub. No.: WO99/47589

PCT Pub. Date: Sep. 23, 1999

(30) Foreign Application Priority Data

Mar. 17, 1998 (FR) .............................................. 98 03234

(51) Int. Cl.[7] .................. A01N 25/02; A01N 25/10; A61L 15/42; A61L 31/00; C08J 3/215
(52) U.S. Cl. .................. 424/405; 424/445; 428/321.5; 514/772.7; 514/937; 514/953; 516/20; 516/30; 523/122
(58) Field of Search ............... 516/20, 30; 523/122; 428/321.5; 514/772.7, 937, 953; 424/405, 445

(56) References Cited

U.S. PATENT DOCUMENTS

| | | | | |
|---|---|---|---|---|
| 4,102,807 A | * | 7/1978 | Iwama et al. ............ 516/30 X |
| 4,857,334 A | * | 8/1989 | Korol et al. ............... 424/445 |
| RE33,048 E | * | 9/1989 | Kimmel et al. ............ 523/122 |
| 4,923,698 A | * | 5/1990 | Rodero ....................... 424/405 |
| 5,045,341 A | * | 9/1991 | Shlenker ............. 428/321.1 X |
| 5,425,955 A | * | 6/1995 | Narayanan ................. 424/405 |
| 5,466,725 A | * | 11/1995 | Kersten et al. ............. 523/122 |
| 5,804,628 A | * | 9/1998 | Busnel et al. .......... 424/405 X |
| 5,883,155 A | * | 3/1999 | Hoerner et al. ............ 523/122 |

FOREIGN PATENT DOCUMENTS

| | | | |
|---|---|---|---|
| EP | 0 771 837 | * | 5/1997 |
| WO | WO 95/17453 | * | 6/1995 |

OTHER PUBLICATIONS

E.K. Lin et al.: "Semicrystalline Diblock Copolymer Platelets on Dilute Solution", Macromolecules, vol. 29, No. 12, pp. 4432–4441, XP 002104880, 1996.*

* cited by examiner

*Primary Examiner*—Richard D. Lovering
(74) *Attorney, Agent, or Firm*—Oblon, Spivak, McClelland, Maier & Neustadt, P.C.

(57) ABSTRACT

The invention concerns stable emulsions, a method for preparing said emulsions and the elastomer films containing them. Said stable emulsions of at least one chemical substance x in an elastomer solution, to be used for preparing an elastomer film, comprise (1) a phase A containing an elastomer dissolved in an organic apolar or slightly polar solvent a, wherein is dispersed (2) a phase B containing at least said chemical substance x, in solution or dispersed in a polar solvent b, non-miscible with phase A and (3) at least a dispersing agent selected from the group consisting of block or grafted polymers. Said emulsions are characterised in that the dispersed phase B droplets have a diameter $\geq 10\,\mu m$; said emulsion comprises, for stabilising said dispersed phase B, besides at least one dispersing copolymer comprising poly A sequences, compatible with phase A and poly B sequences compatible with phase B, at least a particulate stabiliser selected from the group consisting of solid organic compounds of dimension ranging between 30 nm and $10\,\mu m$, or solid mineral compounds of dimension ranging between 5 nm and $10\,\mu m$, whereof the surface state is organophilic; the mass fraction $\phi_B$ of the dispersed phase (phase B) in the emulsion ranges between 0.01 and 0.2; the mass fraction of block or grafted copolymers, $\phi_{CD}$, expressed relative to dispersed phase B ranges between 0.001 and 0.3, preferably between 0.01 and 0.2 and the mass fraction of particulate stabiliser (SP), $\phi_{SP}$, expressed relative to dispersed phase B ranges between 0.001 and 0.5.

61 Claims, 4 Drawing Sheets

STABLE EMULSIONS, PREPARATION METHODS AND APPLICATIONS

This application is a 371 of PCT/FR99/00586 filed Mar. 16, 1999.

The present invention relates to stable emulsions comprising a continuous phase formed from a solution of an elastomer in an organic solvent and a dispersed phase, in the form of droplets with a diameter greater than or equal to 10 μm; said droplets comprise an active chemical substance in a solvent which is immiscible with the elastomer solution and are capable of being converted into elastomeric films.

The present invention also relates to the process for preparing said emulsions, as well as to elastomeric films containing them: said emulsions can give, after evaporation of the solvent for the elastomer, an elastic film containing stable droplets of liquid, with a diameter of greater than or equal to 10 μm.

International patent application WO 95/17453 in the name of the Applicant describes the preparation of a two-phase solid material containing a dispersion of liquid droplets of an active chemical substance, which are stabilized by means of a block or grafted copolymer comprising at least a number of sequences polyB which are compatible with said droplets and a number of polyA sequences, which are immiscible with these droplets, in an elastomer. The droplets generally have a diameter of less than 10 μm. Under these conditions, the block or grafted copolymer effectively stabilizes the emulsion, which is thus distributed homogeneously in said film.

Figure 1:
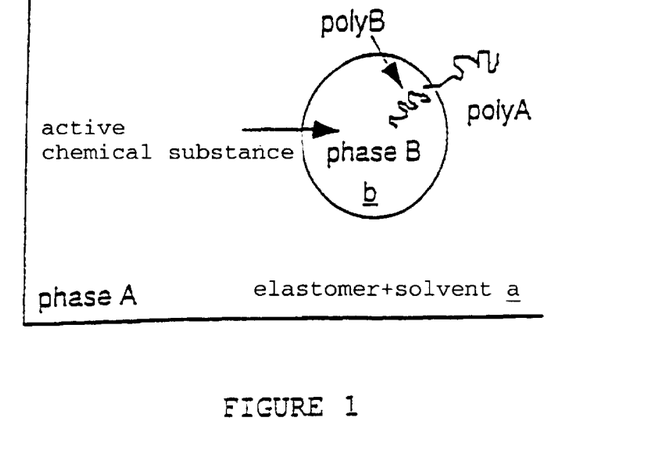
FIG. 1 is a schematic representation of the emulsion in step (1) as described in international PCT patent application WO 95/17453.

That international patent application WO 95/17453 also describes the process for preparing said elastomeric material; this process essentially comprises two steps:

(1) the preparation of an emulsion which comprises:
   the preparation of a phase A by dissolving the elastomer in an organic solvent a (phase A: solution of elastomer in the organic solvent a)
   the preparation of a phase B, by mixing an active chemical substance in an organic solvent b which is immiscible with phase A (phase B: solution or dispersion of active substance in an organic solvent b which is immiscible with the phase A)
   the addition to phase A or phase B, in proportions of from 0.1 to 50%, preferably from 0.1 to 25%, of a block or grafted copolymer comprising at least a number of polyA sequences, which are miscible with the phase A, and a number of polyB sequences, which are miscible with the phase B, as defined above
   the dispersion of phase B in phase A to give an emulsion in which phase A constitutes the continuous phase and phase B constitutes the dispersed phase, as represented in FIG. 1, and (2) evaporation of the organic solvent a to give an elastomeric film containing, in the form of a stable dispersion, droplets of solvent b generally less than 10 μm in diameter, loaded with active chemical substance.

Continuing its research, the Applicant became interested more particularly in improving the stability of emulsions B in A in step (1), in particular those with droplets at least equal to 10 μm in diameter and preferably between 10 and 50 μm in diameter.

The various elastomeric materials usually used in the medical or paramedical field (in particular hygiene) can be modified so as to be combined with active chemical substances, having a protective effect, during the use of this [sic] materials (gloves, fingerstalls, condoms, strips and various dressings). Specifically, both in the case of examination or surgery or in odontology, and for protection against pathogenic agents such as, for example, bacteria, viruses and fungal spores, a rupture or sometimes even simply the pores or a crack in the elastomeric membrane can result in the wearer of said material becoming contaminated by being pricked with syringes, suture needles, trocars, bone splinters, etc.

Now, if the droplets containing the active chemical substance, which may be released in the event of rupture of the protective elastomeric material, do not release a sufficient amount of active substance, the protective effect will not be sufficient.

Moreover, if the diameter of the droplets is increased, so as to allow the release of a sufficient effective amount of active substance to rapidly neutralize the pathogenic agent which may thus have been accidentally introduced into the wearer, the problem of the stability of the emulsion may become crucial.

According to the literature (P. Becher, *Emulsion: Theory and Practice, ACS Monogr.*, 162, 1965), an emulsion can be defined as "a heterogeneous system consisting of at least one immiscible liquid intimately dispersed in another in the form of droplets". These systems generally contain one or more surfactants, like the block or grafted copolymers described in international patent application WO 95/17453. In this case, the particles are subjected to Van der Waals attraction forces and electrostatic or steric repulsion forces associated with the presence of copolymer, as well as to gravitational forces, if the densities of the phases present are different.

The equilibrium between the forces of attraction and repulsion is the origin of stabilization or destabilization of the emulsions.

Two main destabilization mechanisms should be envisaged for these systems:
   flocculation, which is reflected by an aggregation of particles in the form of clusters, and
   coalescence, which is the result of thinning of the liquid film separating the particles and is reflected by fusion of the particles to form a single particle of larger size.

The block or grafted copolymers as described in international patent application WO 95/17453 are particularly suitable for stabilizing emulsions comprising droplets less than or equal to 10 μm in diameter, by reducing the phenomena of coalescence and/or flocculation.

The Applicant has now found that to stabilize droplets of a phase B (containing an active chemical substance x and a solvent b) with a diameter ≧10 μm, dispersed in an organic phase A (elastomer+solvent a), said block or grafted copolymers must be used as a mixture with other compounds of particle-stabilizing type, in order to effectively obtain stabilization of the emulsion.

The Applicant has also found that, when the emulsion comprises certain chemical substances x which have surfactant properties, it is possible to reduce the content of block or grafted copolymer, or even to dispense with it altogether. In such a case, said chemical substance included in phase B and combined with the particulate stabilizer also makes it possible to obtain a stable emulsion.

A subject of the present invention is a stable emulsion of at least one chemical substance x in an elastomer solution, which can be used for the preparation of an elastomeric film, comprising (1) a phase A comprising an elastomer dissolved in an apolar or relatively nonpolar organic solvent a, in which is dispersed (2) a phase B comprising at least said chemical substance x dissolved or dispersed in a polar solvent b, which is immiscible with phase A, and (3) at least one dispersing agent selected from the group consisting of block or grafted copolymers, this emulsion being characterized:

in that the droplets of dispersed phase B have a diameter $\geq 10$ μm, in that said emulsion comprises, for the stabilization of said dispersed phase B, besides at least one block or grafted copolymer (also referred to as dispersing copolymer) comprising polyA sequences which are compatible with phase A and polyB sequences which are compatible with phase B, at least one particulate stabilizer selected from the group consisting of solid organic compounds of between 30 nm and 10 μm in size or solid inorganic compounds of between 5 nm and 10 μm in size, of any geometry (sphere, parallelepiped, finely divided solid, etc.), whose surface is organophilic in nature, in that the mass fraction $\phi_B$ of dispersed phase (phase B) in the emulsion, expressed by:

$$\phi_B = \frac{m_B}{m_B + m_A + m_{elastomer}}$$

is between 0.01 and 0.2,
with $m_B$=mass of phase B (solvent b+active chemical substance x)
$m_A$=mass of solvent a
$m_{elastomer}$=mass of the elastomer dissolved in a;

in that the mass fraction of the block or grafted copolymer (dispersing copolymer, DC), $\phi_{DC}$, expressed relative to the dispersed phase B, i.e.:

$$\phi_{DC} = \frac{m_{DC}}{m_{DC} + m_B}$$

is between 0.001 and 0.3, preferably between 0.01 and 0.2,
with $m_B$=mass of phase B (solvent b+active chemical substance x)
$m_{DC}$=mass of dispersing copolymer; and in that the mass fraction of particulate stabilizer (PS), $\phi_{PS}$, formed in situ or added as an adjuvant, expressed relative to the dispersed phase B, i.e.:

$$\phi_{PS} = \frac{m_{PS}}{m_{PS} + m_B}$$

is between 0.001 and 0.5,
with $m_{PS}$=mass of particulate stabilizer
$m_B$=mass of phase B (solvent b+active chemical substance x).

For reasons of convenience, the proportions of the various constituents of the emulsion are expressed in mass fractions rather than in volume fractions.

Preferably, said mass fraction of the block or grafted copolymer, $\phi_{DC}$, is between 0.001 and 0.2, preferably between 0.01 and 0.1.

The expression "particulate stabilizer whose surface is organophilic in nature" means a solid organic compound, in particular of polymeric type, or a solid inorganic compound, finely divided and dispersible in the continuous phase (phase A); the surface nature can be modified by means of a surface-treating agent, to make said particulate stabilizer organophilic.

In such emulsions, the block or grafted copolymer denoted by dispersing copolymer serves essentially to facilitate the dispersion of one liquid in the other when the emulsion is prepared, by lowering the interface tension between phase A and phase B, and only partially to stabilize the droplets since this stabilization is essentially provided by the particulate stabilizer.

Surprisingly, the combination of a dispersing copolymer and a particulate stabilizer makes it possible to stabilize an emulsion comprising droplets of diameter $\geq 10$ μm. Specifically, in such a case, the particulate stabilizer alone has no dispersing effect and does not allow the emulsion to be prepared; similarly, the dispersing copolymer alone does not stabilize the emulsion sufficiently.

Figure 2:
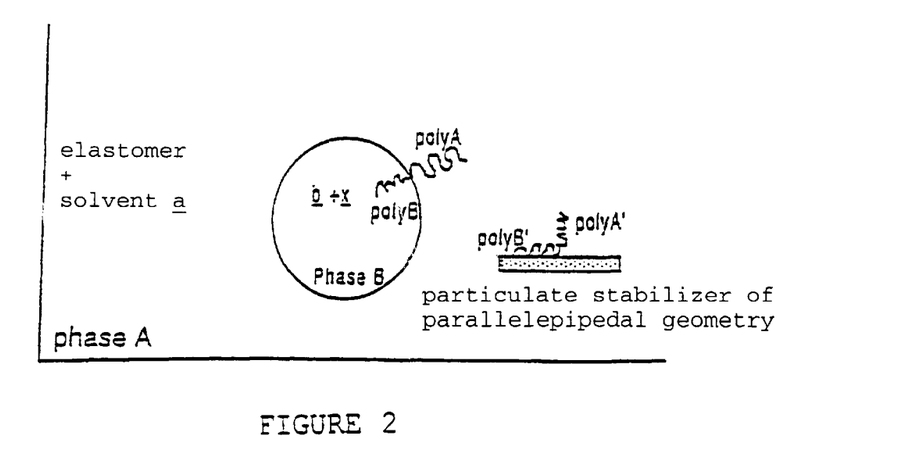
FIG. 2 is a schematic representation of the emulsion according to the invention, the particulate stabilizer being organic or inorganic and of parallelepipedal geometry, the dispersing copolymer being a polyA-polyB diblock copolymer.
Figure 3:
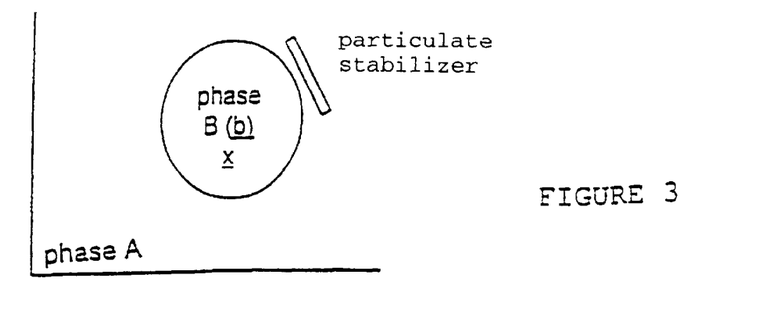
FIG. 3 is a schematic representation of the emulsion according to the invention, in which the chemical substance x acts as dispersing agent.

A synoptic scheme representing a droplet of emulsion stabilized by means of a mixture of dispersing copolymer and a particulate stabilizer is represented in FIG. 2.

In accordance with the invention, when the particulate stabilizer is of organic nature, it is essentially of polymeric type and is selected from the group consisting of organophilic block or grafted copolymers, identical to or different than those used as dispersing copolymers, which are capable of forming structures with a diameter of greater than 30 nm and cellulose derivatives such as microcellulose, starch or certain finely divided polymers; in this case, said particulate stabilizer is:

either naturally organophilic (block or grafted copolymers), on account of the presence of a fleece of polyA sequences at its surface; it can then be:
  formed in situ in the solvent a for phase A; in this case, it is preferably identical to the dispersing copolymer and is selected from block copolymers capable of forming, in addition to "standard" micelles, other set structures, greater than 30 nm in size, such as, for example, structures of "tile" type (detailed in Example 1) or any other copolymer aggregate of less well defined geometry. It is all these combined and set structures which can behave like a particulate stabilizer. Preferably, such a particulate stabilizer is selected from the group consisting of copolymers containing a crystallizable polyB sequence, such as, for example; polyoxyethylene, poly(ethylene), polyamide or polyester such as poly(caprolactone), given that the polyA sequence must be soluble in phase A of the emulsion, or
  added in the form of combined and set structures greater than 30 nm in size, formed by a block copolymer and isolated beforehand from other small structures such as micelles. In this case, the particulate stabilizer can optionally be of a different chemical nature than that of the dispersing copolymer, but is selected from the particulate stabilizers as defined above.

or made organophilic and added as an adjuvant before, during or after formation of the emulsion; it is selected from cellulose derivatives such as microcellulose, starch or certain finely divided polymers;

it is made organophilic by treatment of its surface with a surface-treating agent capable of making it organophilic and thus dispersible in phase A of the emulsion, and of giving it steric-mediated stabilizing properties; the mass fraction of the surface-treating agent used to make the surface of the particles organophilic, i.e. $\phi_{STA}$, expressed relative to the particulate stabilizer, i.e.:

$$\phi_{STA} = \frac{m_{STA}}{m_{PS} + m_{STA}}$$

is between 0.001 and 0.5,
with $m_{STA}$=mass of the surface-treating agent
$m_{PS}$=mass of particulate stabilizer.

Preferably, said mass fraction of the surface-treating agent, $\phi_{STA}$, is between 0.001 and 0.1.

Also in accordance with the invention, when the particulate stabilizer is of inorganic type, this stabilizer is chosen from the group which comprises clays, silicas, talc, kaolin and derivatives of these products and is surface-treated with a surface-treating agent which is capable of making it organophilic and thus dispersible in the continuous phase (phase A) of the emulsion, and of giving it steric-mediated stabilizing properties, and is added, as an adjuvant, to phase A containing the solution of elastomer in solvent a and the dispersing copolymer; the mass fraction of surface-treating agent relative to the particulate stabilizer for the emulsion is between 0.001 and 0.5, as specified above.

Preferably, said mass fraction of the surface-treating agent, $\phi_{STA}$, is between 0.001 and 0.1.

Figure 4:
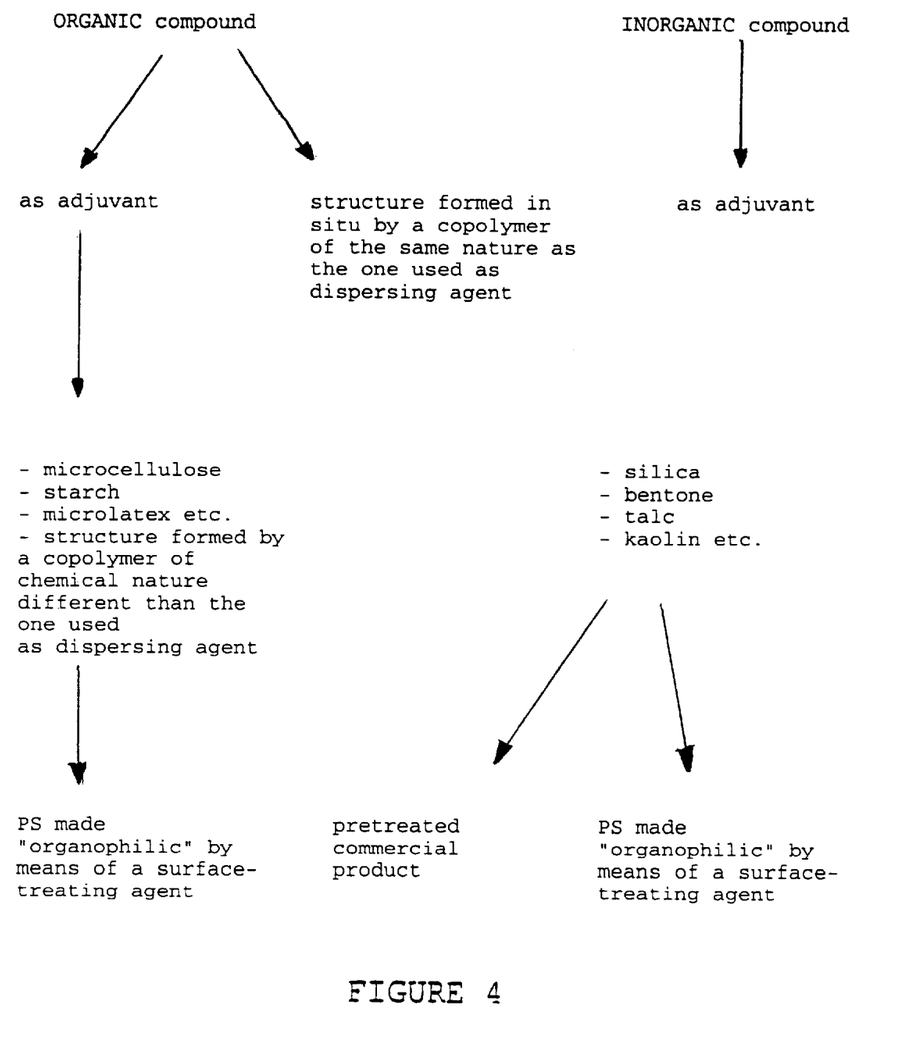
FIG. 4 represents the various options of particulate stabilizer (PS): finely divided organic or inorganic solid.

As a variant, the inorganic particulate stabilizer can be chosen from commercially available "organophilic" products, such as, for example, certain organophilic silicas or clays (Bentone 38, Bentone SD-1, Rheox Inc., etc.), and consequently does not require any additional surface-treating agent. These various possibilities-are summarized in FIG. 4.

According to one advantageous embodiment of said emulsion, it comprises several particulate stabilizers, such as, for example, the combination of a particulate stabilizer formed in situ during the dissolution of the dispersing copolymer with a second particulate stabilizer in the form of an adjuvant.

According to another advantageous embodiment of said emulsion, the dispersing block copolymer is selected from diblock copolymers of polyA-block-polyB type, triblock copolymers of polyB-block-polyA-block-polyB (BAB) type, of polyA-block-polyB-block-polyA (ABA) type, of polyA-block-polyB-block-polyC (ABC) type or of polyA-block-polyC-block-polyB (ACB) type, or more generally from multiblock compounds containing polyA, polyB and polyC sequences and the copolymer of the grafted dispersing type is selected from compounds of polyA-grafted-polyB type, polyB-grafted-polyA type, polyA-grafted-polyB and polyC type or polyC-grafted-polyA and polyB type.

The proportions of polyA sequence, expressed by mass relative to the sum of the polyA+polyB sequences, are between 10 and 90%, and the proportions of polyB sequences are between 90 and 10%, and the mass proportions of polyC sequences are between 0 and 50% relative to all of the sequences.

The molar masses of the polyA, polyB and polyC sequences are between 1000 and 500,000 daltons.

In accordance with the invention, the polyA sequences, which are compatible with the apolar or relatively nonpolar solvent a, are selected from the group consisting of polydienes, polyolefins, polyethers and silicones, such as polyisoprene, polybutadiene, polyisobutene, hydrogenated polybutadiene or hydrogenated polyisoprene, poly(4-tert-butylstyrene), polyoxypropylene, polyoxybutylene, polydimethylsiloxane, poly(2-ethylhexyl methacrylate) or poly(lauryl methacrylate), which are miscible with a solution of elastomer in a solvent a, the polyB sequences, which are compatible with the solvent b, are selected from the group consisting of polyoxyethylene, polyvinylpyrrolidone, polyacrylic acids, poly(vinyl alcohol) and quaternized poly(vinylpyridine).

The polyC sequences can be chosen from the group which comprises polymers which may be either compatible with the solvent a or the solvent b, or incompatible with the solvents a and b. The polyC sequence is chosen, in a non-limiting manner, from the group formed by acrylic or vinyl polymers such as poly(methyl methacrylate) or polystyrene.

According to another advantageous embodiment of said emulsion, the surface-treating agent, which is capable of making the particulate stabilizer organophilic, is selected from the group consisting of block or grafted copolymers containing at least one polyA' sequence which is soluble in the solvent a, and a polyB' sequence capable of being adsorbed onto or binding to the surface of the particulate stabilizer, said polyA' and polyB' sequences being identical to or different than the polyA and polyB sequences and functionalized oligomers of polyA'-F type, in which F is a chemical function capable of being adsorbed onto the particulate stabilizer.

In accordance with the invention,, the polyA' sequences are chosen from polymers which are soluble in the apolar or relatively nonpolar solvent a, such as, for example, from the group which comprises polydienes, polyolefins, polyethers and silicones, such as polyisoprene, polybutadiene, polyisobutene, hydrogenated polybutadiene or hydrogenated polyisoprene, poly(4-tert-butylstyrene), polyoxypropylene, polyoxybutylene, polydimethylsiloxane, poly(2-ethylhexyl methacrylate) or poly(lauryl methacrylate), which are miscible with a solution of elastomer in a solvent a, and the polyB' sequences are chosen from polymers capable of being adsorbed onto the surface of the particulate stabilizer, and is chosen from the group which comprises polyoxyethylene, polyvinylpyrrolidone, polyacrylic acids, poly(vinyl alcohol) and quaternized or non-quaternized poly(vinylpyridine).

According to another advantageous embodiment of the emulsion, the proportions of polyA' sequence, expressed by mass relative to the sum of the polyA'+polyB' sequences, are between 10 and 90%, preferably between 20 and 80%, and the proportions of polyB' sequences are between 90 and 10%.

According to yet another advantageous embodiment of said emulsion, the molar masses of the polyA' and polyB' sequences are between 150 and 200,000 daltons.

According to another advantageous embodiment of said emulsion, F is selected from the group consisting of acid, amine or alcohol functions and groups capable of reacting chemically with the surface of the particulate stabilizer, such as, for example, epoxy, isocyanate or aziridine groups.

Such emulsions of an active chemical substance x in an elastomer solution comprise droplets which have a diameter greater than or equal to 10 $\mu$m and very good stability imparted jointly by said block or grafted copolymer and by said particulate stabilizer made organophilic by means of a surface-treating agent as defined above.

The stability of said emulsions can be evaluated by detecting the phenomena of coalescence and flocculation, as well as by monitoring the diameter of the droplets over time.

The elastomer, the solvent a, the active chemical substance x and the solvent b are, in particular, those described in international patent application WO 95/17453.

For example:
the elastomer is selected, in a non-limiting manner, from the group consisting of polybutadiene, polyisoprene, polychloroprene, SBR (styrene butadiene rubber) copolymers, NBR (nitrile butadiene rubber) copolymers, SBS (styrene butadiene styrene) copolymers, SIS (styrene isoprene styrene) copolymers, SEBS (styrene ethylene-co-butylene styrene) copolymers, alone or as a mixture with one or more plasticizers or flexibilizing agents.

the apolar or relatively nonpolar solvent a is chosen in particular from aliphatic, aromatic and alicyclic hydrocarbons, for example methylcyclohexane, toluene, heptane or a mixture thereof.

the active chemical substance x is selected from compounds capable of bringing about virtually instantaneous denaturing of proteins by means of simple contact, either by chemical reaction or by a physicochemical effect such as a modification of the surface tension. This family of compounds comprises, inter alia, biocides, such as quaternary ammoniums, preferably dimethyldidecylammonium chloride, biguanides, phthalaldehyde, phenolic or benzylic derivatives, formaldehyde, nonionic surfactants comprising at least one polyoxyethylene sequence, hexamidine, iodine-containing polyvinylpyrrolidone compounds, nonionic surfactants with virucide activity, and sodium and potassium dichromates and hypochlorites, used alone or as a mixture.

the solvent b is immiscible with the solvent a as defined above. b is selected, for example, from polyols, and preferably glycerol, ethylene glycol and polyethylene glycols which are liquid at room temperature and have a molar mass of between 62 (ethylene glycol) and 750 daltons (PEG-750), but can be any other compound which is immiscible with the solvent a, such as, for example, water, dimethyl sulfoxide, formamide or ethanolamine or mixtures of such solvents.

Preferably, the mass fraction of the active chemical substance x, i.e. $\phi_x$, in the emulsion described above is expressed by $$\phi_x = \frac{m_x}{m_x + m_b} = \frac{m_x}{m_B}$$

and is between 0.01 and 0.7, preferably between 0.1 and 0.4,
with $m_x$=mass of active chemical substance x
$m_b$=mass of solvent b
$m_B$=mass of dispersed phase B.

As a variant, if the active chemical substance x has surfactant properties, i.e. if it allows the interface tension between phase A and phase B to be reduced, which is the case in particular for quaternary ammoniums, nonionic surfactants comprising at least one polyoxyethylene sequence and nonionic surfactants with virucide activity, this active chemical substance x can act as a dispersant. The result of this is that, under these conditions, it is possible to reduce the content of block or grafted copolymer in the emulsion described above, or even to dispense with it altogether, thus simplifying the formulation of the emulsion according to the invention while still providing suitable stabilization of the droplets with a diameter $\geq 10\ \mu m$.

A subject of the present invention is thus also a stable emulsion of at least one chemical substance x in an elastomer solution, which can be used, to prepare an elastomeric film, comprising (1) a phase A comprising an elastomer dissolved in an apolar or relatively nonpolar organic solvent a, in which is dispersed (2) a phase B comprising at least said chemical substance x, dissolved or dispersed in a polar solvent b, which is immiscible with the phase A, this emulsion being characterized:

in that the droplets of dispersed phase B have a diameter $\geq 10\ \mu m$, in that said emulsion comprises, to stabilize said dispersed phase B, (1) at least one chemical substance x, this substance having surfactant properties and acting as a dispersant, said chemical substance x being selected from the group consisting of quaternary ammoniums, nonionic surfactants comprising at least one polyoxyethylene sequence and nonionic surfactants with virucide activity, and (2) at least one particulate stabilizer as defined above, preferably formed from a block or grafted copolymer, in that the mass fraction $\phi_B$ of the dispersed phase (phase B) in the emulsion, expressed by:

$$\phi_B = \frac{m_B}{m_B + m_A + m_{elastomer}}$$

is between 0.01 and 0.2,
with $m_B$=mass of phase B (solvent b+active chemical substance x)
$m_A$=mass of solvent a
$m_{elastomer}$=mass of the elastomer dissolved in a;

in that the mass fraction of the active chemical substance x, i.e. $\phi_x$, expressed by $$\phi_x = \frac{m_x}{m_x + m_b} = \frac{m_x}{m_B}$$

is between 0.01 and 0.7, preferably between 0.1 and 0.4,
with $m_x$=mass of active chemical substance x
$m_b$=mass of solvent b
$m_B$=mass of dispersed phase B, in that the mass fraction of particulate stabilizer (PS), $\phi_{PS}$, formed in situ or added as an adjuvant, expressed relative to the dispersed phase B:

$$\phi_{PS} = \frac{m_{PS}}{m_{PS} + m_B}$$

is between 0.001 and 0.5,
with $m_{PS}$=mass of particulate stabilizer
$m_B$=mass of phase B.

Advantageously, said elastomer, said solvent a, said solvent b and said particulate stabilizer are as defined above in the context of the emulsions comprising a dispersing agent selected from the group consisting of block or grafted copolymers.

Surprisingly, the combination of the active chemical substance x with surfactant properties and the particulate stabilizer(s) preferably when these are block or grafted copolymers as defined above, makes it possible to stabilize an emulsion comprising droplets with a diameter $\geq 10\ \mu m$.

A subject of the invention is also a process for preparing said stable emulsion:

I. When the particulate stabilizer is added before the formation of the emulsion, this formation is carried out as follows:

the preparation of a phase A by dissolving the elastomer in an organic solvent a (phase A: solution of elastomer in the organic solvent a), the preparation of a phase B, by mixing an active chemical substance x in an organic solvent b which is immiscible with phase A (phase B: solution or dispersion of active substance in an organic solvent b which is immiscible with phase A), the addition to phase A or phase B, in proportions as defined above, of a block or grafted copolymer serving essentially as a dispersing copolymer; however, if this copolymer is capable of forming in situ, in phase A, in addition to a standard organization of micellar type, other combined and set structures with a diameter of greater than 30 nm, which can act as particulate stabilizer, the latter no longer needs to be added in a subsequent step; when said copolymer comprises a crystallizable polyB sequence, it is effectively capable of forming in situ, in phase A, in addition to a standard organization of micellar type, other combined and set structures which can act as particulate stabilizer. In the opposite case, the addition to phase A of the mass fraction of the particulate stabilizer, as defined above, is carried out in a second stage, in the form of an adjuvant. This solid organic or inorganic compound is organophilic and thus, if necessary, is pretreated with a surface-treating agent, as specified above, and the dispersion of phase B in phase A, to obtain an emulsion in which phase A constitutes the continuous phase and phase B constitutes the dispersed phase.

When the active chemical substance x acts as a dispersing agent, the process for preparing the emulsion is carried out as follows, when the particulate stabilizer is added before formation of the emulsion:

the preparation of a phase A by dissolving the elastomer in an organic solvent a (phase A: solution of elastomer in the organic solvent a), the preparation of a phase B, by mixing the active chemical substance x of surfactant nature in an organic solvent b which is immiscible with phase A (phase B: solution or dispersion of active substance in an organic solvent b which is immiscible with phase A), the addition to phase A or phase B, in proportions as defined above, of an organophilic particulate stabilizer or one which has been made organophilic, preferably formed from a block or grafted copolymer, the dispersion of phase B in phase A to obtain an emulsion in which phase A constitutes the continuous phase and phase B constitutes the dispersed phase.

II. When the particulate stabilizer is added after formation of the emulsion, this formation is carried out as follows:

the preparation of a phase A by dissolving the elastomer in an organic solvent a (phase A: solution of elastomer in the organic solvent a), the preparation of a phase B, by mixing an active chemical substance x in an organic solvent b which is immiscible with phase A (phase B: solution or dispersion of active substance in an organic solvent b which is immiscible with phase A), the addition to phase A or phase B, in proportions as defined above, of a block or grafted copolymer serving essentially as a dispersing copolymer, the dispersion of phase B in phase A to obtain an emulsion in which phase A constitutes the continuous phase and phase B constitutes the dispersed phase, the addition, with stirring, of the organophilic particulate stabilizer as defined above.

When the active chemical substance x acts as a dispersing agent, the process for preparing the emulsion is carried out as follows, when the particulate stabilizer is added before or after formation of the emulsion:

the preparation of a phase A by dissolving the elastomer in an organic solvent a (phase A: solution of elastomer in the organic solvent a), the preparation of a phase B, by mixing the active chemical substance x of surfactant nature in an organic solvent b which is immiscible with phase A (phase B: solution or dispersion of active substance in an organic solvent b which is immiscible with phase A), the dispersion of phase B in phase A to obtain an emulsion in which phase A constitutes the continuous phase and phase B constitutes the dispersed phase, and the simultaneous or non-simultaneous addition, with stirring, of the particulate stabilizer which is organophilic or which has been made organophilic, preferably formed from a block or grafted copolymer.

As a variant, the particulate stabilizer is added before formation of the emulsion, i.e. when phase B is dispersed in phase A.

As a variant, the particulate stabilizer can be made organophilic directly by the copolymer used to disperse the emulsion.

Figure 5:
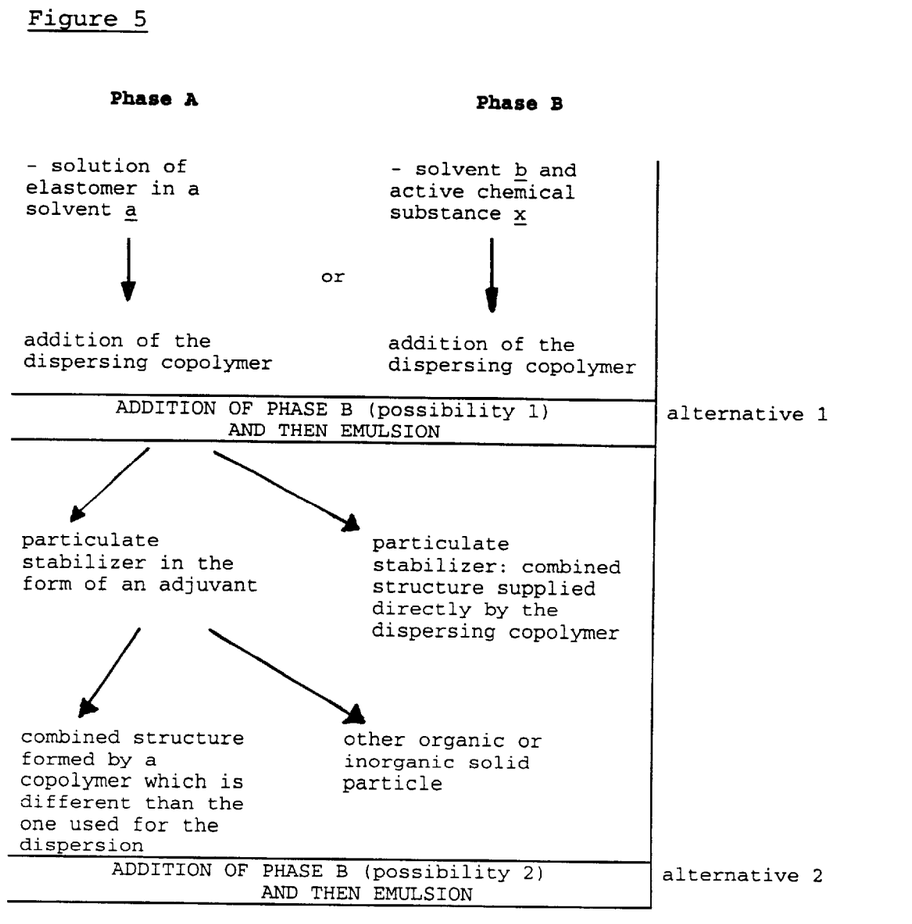
FIG. 5 illustrates a diagram of the various alternatives for preparing the emulsions according to the invention.

These various alternatives are summarized in FIG. 5.

A subject of the present invention is also an elastomeric film, characterized in that it is obtained by evaporating the solvent a from an emulsion as defined above.

Such an elastomeric film, which can advantageously serve as a protective support, comprises stable droplets of a solvent b which is immiscible with the elastomer, loaded with at least one active substance x, these droplets having a diameter $\geq 10$ $\mu$m and being uniformly distributed throughout the elastomeric material.

In accordance with the invention, the combination of at least one block or grafted copolymer and at least one particulate stabilizer makes it possible to obtain the stability of the emulsion both in the presence of the solvent a and during the evaporation of said solvent a, i.e. during the formation of the film, which, itself, is stable and has optimum mechanical properties.

The subject of the present invention is also a process for preparing said elastomeric film, characterized in that it comprises:

(a) the preparation of an emulsion as defined above, and (b) the evaporation of the organic solvent a to obtain an elastomeric film containing, in the form of a stable dispersion, droplets of solvent b, loaded with active chemical substance x, with a diameter $\geq 10$ $\mu$m.

A subject of the present invention is also the various uses of the elastomeric film according to the invention, more particularly in the medical and paramedical fields: gloves, fingerstalls, condoms or dressings comprising an elastomeric film in accordance with the invention.

BRIEF DESCRIPTION OF THE DRAWINGS

In addition to the arrangements hereinabove, the invention also comprises other arrangements, which will emerge on reading the description which follows, with reference to examples of implementation of the process which is the subject of the present invention and to the attached drawings, in which:

FIG. 6 represents a schematic structure in "tiles" of a copolymer containing a crystalline polyB sequence which is insoluble in the solvent a, and a polyA sequence which is soluble in a;

It should be clearly understood, however, that these examples are given purely for the purpose of illustrating the subject of the invention, of which they do not in any way constitute a limitation.

EXAMPLE 1
Evaluation of the Stability and Diameter of the Emulsions Obtained According to the Invention The stability and diameter of the emulsions are evaluated under the conditions specified below, bearing in mind the parameters which follow.

An emulsion as defined in the present invention is subjected to several forces, namely:
  forces of attraction between the droplets, which can give rise to flocculation and/or coalescence;
  forces of repulsion between the droplets, by means of the presence of the copolymer adsorbed onto their surface and by means of the presence of the organophilic particulate stabilizer which reduces the collisions between the droplets.

It is the presence of the forces of repulsion which makes it possible to slow down or even avoid the phenomena of coalescence and/or flocculation.

By definition, an emulsion will be considered as stable when it does not coalescence or flocculate.

The stability of the emulsions is evaluated by means of two complementary techniques:
  by direct monitoring of the phenomena of flocculation and/or coalescence using a device which operates by scattering and back-scattering light (device sold by the company Formulaction under the name Turbiscan MA1000). The appearance of destabilization phenomena is detected by a change in the signal transmitted or back-scattered by the emulsion.
  by monitoring the average diameter over time: if the emulsion is perfectly stable, the diameter is constant over time. On the other hand, it increases under the effect of flocculation or coalescence of the droplets.

To do this, the diameter of the emulsion is measured by the technique of photosedimentation on an aliquot portion of the emulsion, on a machine of the Shimadzu SA-CP3 type.

This technique allows access to the size distribution of the emulsion. In this study, the diameter of the emulsion will be expressed by the modal diameter of the particles, which corresponds to the maximum of the distribution curve.

EXAMPLE 2
Emulsion Prepared in the Presence of a Polybutadiene-polyoxyethylene Diblock Copolymer, Referred to as PBut-POE (dispersing copolymer) and an Organic Particulate Stabilizer Formed in Situ from this Diblock Copolymer: Comparison with the Characteristics of the Emulsion Obtained in the Absence of Particulate Stabilizer In this example, the particulate stabilizer corresponds to a set structure formed in situ by a fraction of the dispersing copolymer dissolved in the solvent a.

The preparation of a stable emulsion of high particle size in accordance with the invention is carried out as follows:

Preparation of the Continuous Phase (phase A):

Synthetic SEBS (polystyrene-poly(ethylene/co/butylene)-polystyrene triblock copolymer) with a molar mass of 85,000 daltons and containing 29% by mass of polystyrene, sold by the company Shell under the name Kraton G 1652, is dissolved, with stirring, so as to obtain a solution containing 20% by weight of SEBS.

Preparation of the Dispersed Phase (phase B):

Bardac (dimethyldidecylammonium chloride) is dissolved, with stirring, in polyethylene glycol with a molar mass of 400 daltons (PEG-400) so as to obtain a solution containing 30% by mass of Bardac.

Preparation of the Solution Comprising the Dispersing Copolymer and the Particulate Stabilizer:

A polybutadiene-polyoxyethylene diblock copolymer, referred to as PBut-POE, was synthesized by anionic polymerization (M. Gervais et al., *Makromol. Chem.*, 1977, 178, 1577–1593). Its content by mass of POE (determined by $^1$H NMR) is 60% and its total molar mass is 10,000 daltons.

The dissolution of the copolymer is carried out according to a protocol commonly described in the literature (E. K. Lin et al. *Macromolecules*, 1996, 29, 4432–4441). In this example, 10 grams of this copolymer are dissolved in 90 grams of methylcyclohexane.

After dissolving the copolymer, two types of structure are formed:
  micelles, formed of a POE "core" and a PBut "crown". Their presence was demonstrated by photon correlation spectroscopy. These structures have surfactant activity and make it possible to subsequently promote the dispersion of phase B in phase A.
  rigid aggregates of parallelepipedal shape and with dimensions of between 0.5 and 2 μm, formed of a POE central portion and PBut "fleece" were revealed by optical microscopy and atomic force microscopy. They can be represented in FIG. 6.

The formation of such structures is explained essentially by the crystalline nature of the POE sequence.

The aggregates represent 60% by mass of the initial copolymer, and can be separated from the micelles, if need be, by centrifugation, and then taken up in methylcyclohexane so as to form a solution of given concentration therein.

Formation of the Emulsion of B in A:

6 grams of the copolymer solution containing the micelles (dispersing copolymer) and,the aggregates (particulate stabilizer) in methylcyclohexane (solution at a concentration of 10% by mass) are added to 100 grams of the SEBS solution. This solution contains 0.24 gram of copolymer in the form of dispersing copolymer (micelles) and 0.36 gram in the form of particulate stabilizer (aggregates). As a variant, it is possible to add the micelles and then the particulate stabilizer separately, the latter having been separated from the micelles and then taken up in methylcyclohexane.

The mixture is homogenized and 12 grams of phase B are then added with stirring.

The mass fractions of phase B and of each of the constituents are summarized below:

$\phi_B=0.102$ $\phi_{DC}=0.020$ $\phi_{PS}=0.029$ $\phi_{STA}=0$

After stirring for 15 minutes under low-shear conditions and at 25° C., an emulsion with a modal diameter of 20 μm is obtained.

Figure 7:
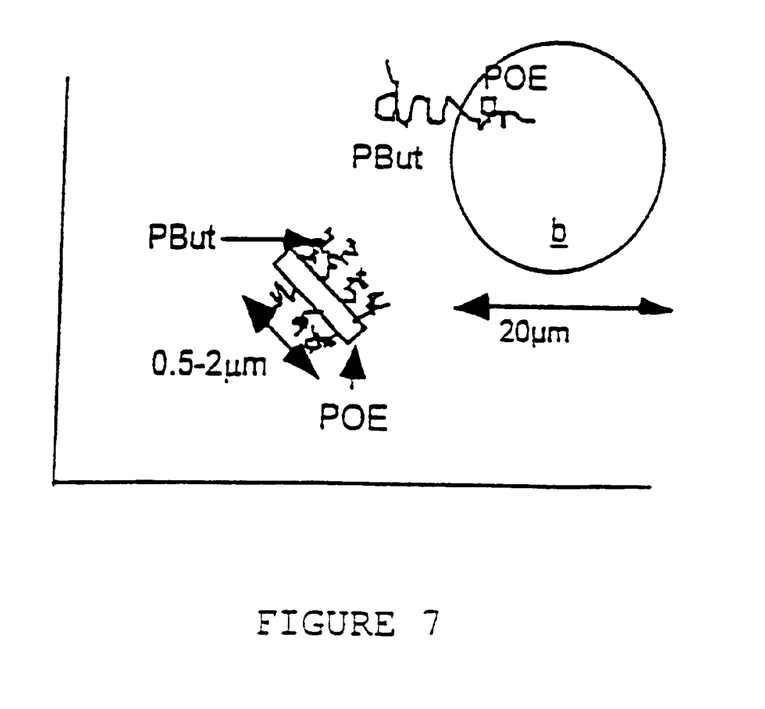
FIG. 7 represents the stabilization of an emulsion by an organic particulate stabilizer (combined structure of tile type formed by a PBut-POE copolymer), and by a dispersing copolymer whose chemical nature is identical to that of the particulate stabilizer.

The schematic structure of this emulsion is represented in FIG. 7.

The stability of this emulsion, i.e. the absence of coalescence and flocculation phenomena, was demonstrated using the Turbiscan MA1000 machine.

As a variant, the particulate stabilizer can be added, with gentle stirring, after emulsifying phase B in phase A, the copolymer in micellar form serving as dispersing agent.

The characteristics of the emulsion are unchanged.

By replacing the particulate stabilizer with an equivalent amount of copolymer in the form of micelles, the emulsion formed has a modal diameter of 7 μm and is not stable, as indicated by the study with the Turbiscan MA1000 machine (decrease in the back-scattering signal over time).

EXAMPLE 3

Emulsion Prepared in the Presence of a Poly(4-tert-butylsytrene)-polyoxyethylene Diblock Copolymer, Referred to as P'BuSt-POE (dispersing copolymer), and of an Organic Particulate Stabilizer Formed in Situ from this Diblock Copolymer In this example, the PBut-POE copolymer is replaced with a poly(4-tert-butylstyrene)-polyoxyethylene diblock copolymer, referred to as P'BuSt-POE, containing 45% by mass of POE (determined by $^1$H NMR) and with a total molar mass of 7700 daltons.

Figure 6:
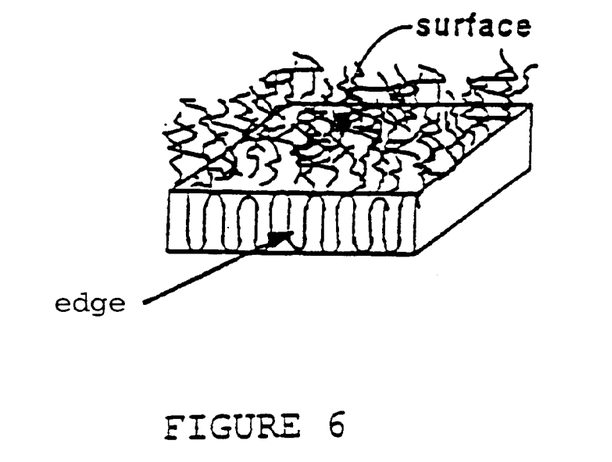

This copolymer is dissolved in methylcyclohexane (solution at a concentration of 10% by mass, formed from 10 grams of copolymer in 90 grams of solvent a), and a mixture of micelles and aggregates forms therein, these aggregates being of parallelepipedal shape and composed of a crystalline POE central structure and P'BuSt "fleece" (see FIG. 6). Their size, evaluated by optical microscopy, is between 1 and 3 μm. These aggregates represent 50% by mass of the initial copolymer, and act in this case as particulate stabilizer. The P'BuSt "fleece" allows the dispersion of the particulate stabilizer in the solvent a, such that it is not necessary to use a surface-treating agent.

The preparation method is similar to that described in Example 2, namely:

preparation of a dissolution of SEBS containing 15% by mass of SEBS in methylcyclohexane preparation of phase B by mixing Bardac and PEG-400 in a 3:7 proportion by mass Formation of the emulsion of B in A:

6 grams of the solution containing the micelles and the aggregates (particulate stabilizer) in methylcyclohexane (10% solution) are added to 100 grams of SEBS solution. The mixture is homogenized, followed by addition, with stirring, of 12 grams of phase B.

The mass fractions of phase B and of each of the constituents are summarized below:

$\phi_B=0.102$ $\phi_{DC}=0.024$ $\phi_{PS}=0.024$ $\phi_{STA}=0$

After stirring for 15 minutes under low-shear conditions and at 25° C., a stable emulsion with a modal diameter of 30 μm is obtained. Monitoring of the stability of the emulsion by means of the Turbiscan MA1000 machine demonstrates the absence of flocculation and coalescence phenomena.

EXAMPLE 4

Emulsion Prepared in the Presence of a Hydrogenated Polybutadiene-polyoxyethylene Diblock Copolymer, Referred to as HPBut-POE, (dispersing copolymer) and an Organic Particulate Stabilizer Formed in Situ from this Diblock Copolymer: Monitoring of the Diameter of the Emulsion as a Function of Time This example is similar to Examples 2 and 3 described above. The dispersing copolymer is an HPBut-POE diblock copolymer containing 50% by mass of POE (determined by $^1$H NMR) and with a total molar mass of 8300 daltons.

This copolymer is dissolved in methylcyclohexane (solution at a concentration of 10% by mass, formed from 10 grams of copolymer in 90 grams of solvent a), and a mixture of micelles and aggregates is formed therein, these aggregates representing about 75% by mass of the initial copolymer, and act in this case as the particulate stabilizer.

The preparation method is similar to the one described in Example 2.

Formation of the Emulsion of B in A:

6 grams of the solution containing the micelles and aggregates (particulate stabilizer) in methylcyclohexane (10% solution) are added to 100 grams of an SEBS solution identical to the one used in the above example. The mixture is homogenized, followed by addition, with stirring, of 12 grams of phase B.

The mass fractions of phase B and of each of the constituents are summarized below:

$\phi_B=0.102$ $\phi_{DC}=0.012$ $\phi_{PS}=0.036$ $\phi_{STA}=0$

After stirring for 15 minutes under low-shear conditions and at 25° C., a stable emulsion with a modal diameter of 22 μm is obtained. The diameter of the emulsion was measured over time. To do this, the emulsion is stored under "static" conditions in a hermetically sealed tube and then stirred slowly before the measurement, so as to homogenize the emulsion throughout the tube and to take a representative sample.

The modal diameter of the emulsion is represented as a function of time in the table below:

| time (hours) | 0 | 2 | 6 | 9 | 24 |
|---|---|---|---|---|---|
| modal diameter (μm) | 23.5 | 22.5 | 22.7 | 23.0 | 23.9 |

To within the uncertainties associated with the analysis, the diameter of the droplets did not change over time, which demonstrates that the emulsion did not coalesce or flocculate.

EXAMPLE 5

Emulsion Prepared in the Presence of a Grafted Copolymer (dispersing polymer) and an Inorganic Particulate Stabilizer of Silica Type.

In this example, the dispersing copolymer is a grafted copolymer of polyethersiloxane type sold by the company Goldschmidt A.G. under the name Tegopren 5840.

The particulate stabilizer is the silica sold by the company Degussa. This compound can be organized either in the form of primary particles (spheres 12 nm in diameter, according to Degussa), or in the form of combinations of these particles, of less defined structure and of larger size. Finally, this silica underwent a chemical treatment performed at the premises of the supplier, in order to make it dispersible in aliphatic solvent.

Consequently, this product will be used in its present form, without addition of any other surface-treating agent.

Preparation of the Continuous Phase (phase A):

Phase A consists of a solution of SEBS Kraton G1652 at a concentration of 15% in methylcyclohexane.

Phase B is identical to the one used in Examples 1 and 2.

Formation of the Emulsion of B in A:

2 grams of Tegopren 5840 are added to 100 grams of the SEBS solution, followed by addition, with stirring, of 1 gram of silica (particulate stabilizer).

20 grams of phase B are then added to this solution, with low-shear stirring.

The mass fractions of phase B and of each of the constituents are summarized below:

$\phi_B$=0.167

$\phi_{DC}$=0.090

$\phi_{PS}$=0.047

$\phi_{STA}$=0(*)

(*): the surface-treating agent is supplied directly by the supplier.

After stirring for 15 minutes under low-shear conditions, a stable emulsion with a modal diameter of 15 μm is obtained.

Advantageously, the viscosity of the emulsion at low shear is increased by the presence of organophilic silica, which reduces the rate of sedimentation of phase B.

Analysis of the scattering and back-scattering profiles of this emulsion by means of the Turbiscan MA1000 machine demonstrates that there is no coalescence or flocculation.

EXAMPLE 6

Emulsion Prepared in the Presence of a P'BuSt-POE Diblock Copolymer (dispersing copolymer) and an Inorganic Particulate Stabilizer of Clay Type In this example, the dispersing copolymer is a P'BuSt-POE block copolymer whose characteristics are similar to those of the copolymer used in Example 3.

After dissolution in methylcyclohexane (solution at a concentration of 10% by mass), micelles and other associated structures are formed. These associated structures are separated from the micelles by centrifugation and represent 50% by mass of the copolymer. The micelles form a solution at a concentration of 5% by mass in methylcyclohexane.

The particulate stabilizer is an organophilic clay of Claytone AF type sold by the company Laporte Absorbants. Its structure is of lamellar type and its sizes are of the order of a micrometer.

As in the above example, this particulate stabilizer is made organophilic by the supplier by means of chemical treatment (binding of a quaternary ammonium bearing alkyl functions to the surface of the clay), and will thus be used in its present form.

Preparation of the Continuous Phase (phase A):

Phase A consists of a solution of SEBS Kraton G1652 at a concentration of 15% in methylcyclohexane.

Phase B is identical to the one used in Examples 1 to 3.

Formation of the Emulsion of B in A:

20 grams of copolymer solution in the form of micelles in methylcyclohexane (5% by mass) are added to 100 grams of the SEBS solution, followed by addition, with stirring, of 0.5 gram of Claytone AF (particulate stabilizer).

20 grams of phase B are then introduced with low-shear stirring.

The mass fractions of each of the phases and of the constituents are summarized below:

$\phi_B$=0.144

$\phi_{DC}$=0.05

$\phi_{PS}$=0.024

$\phi_{STA}$=0(*)

(*): the surface-treating agent is supplied directly by the supplier.

After stirring for 15 minutes under low-shear conditions, a stable emulsion with a modal diameter of 15 μm is obtained.

Advantageously, the addition of organophilic clay is reflected by an increase in the viscosity at very low shear or at rest. Just as in Example 5 above, analysis of the scattering and back-scattering profiles of this emulsion using the Turbiscan MA1000 machine demonstrates that there is no coalescence or flocculation.

EXAMPLE 7

Preparation of an Emulsion from a Solution of P'BuSt-POE Copolymer Containing Micelles and Aggregates, and a Second Particulate Stabilizer of Clay Type This example is a variant of Example 6 described above.

In this case, the crude copolymer solution, i.e. the solution containing the micelles and aggregates, is introduced in its present form into phase A.

Thus, two types of particulate stabilizer are finally present in the solution: the organophilic clay and the aggregates formed by the copolymer.

The emulsion is prepared in a manner similar to that described in Example 6, i.e.:

by addition of the copolymer solution containing the micelles and aggregates to the SEBS solution, then by addition, with stirring, of the organophilic clay, and finally by addition, under low shear, of phase B If the amount of dispersing copolymer (i.e. $\phi_{DC}$) is identical to that used in the above example, the emulsion has similar properties (diameter, stability).

If the total amount of copolymer introduced is identical to that of Example 6 (in this case a fraction of the copolymer in the form of micelles was replaced with aggregates), the emulsion which is formed has a larger diameter (20–25 μm) while at the same time being stable.

EXAMPLE 8

Emulsion Prepared in the Presence of an Active Chemical Substance x which Acts as Dispersing Agent and an Organic Particulate Stabilizer Consisting of Set Structures of a Hydrogenated Polybutadiene-poly(oxyethylene) Diblock Copolymer In this example, the dispersing copolymer, whose role is to lower the surface tension between phase A and phase B, is replaced with a chemical substance x which has both virucidal activity and surfactant properties similar to those of the copolymer. This chemical substance, introduced directly into phase B, is ethoxylated nonylphenol, sold by the company Union Carbide under the name Triton X100.

The particulate stabilizer is an HPBut-POE block copolymer containing 50% by mass of POE, whose properties are similar to the one used in Example 4. This copolymer is dissolved in methylcyclohexane (solution at a concentration of 10% by mass, formed from 10 grams of copolymer in 90 grams of solvent a), and forms a mixture of micelles and aggregates therein, these aggregates representing about 75% by mass of the initial copolymer. The aggregates are separated from the micelles by centrifugation and taken up in methylcyclohexane so as to form a 5% solution therein.

The preparation of a stable emulsion of high particle size in accordance with the invention is carried out as follows:

Preparation of the Continuous Phase (phase A):

Phase A consists of a solution of SEBS Kraton G1652 at a concentration of 15% in methylcyclohexane.

Preparation of the Dispersed Phase (phase B):

Triton X100 is dissolved, with stirring, in polyethylene glycol of molar mass 400 daltons (PEG-400) so as to obtain a solution containing 30% by mass of Triton X100.

Formation of the Emulsion of B in A:

20 grams of solution of copolymer in the form of aggregates in methylcyclohexane (5% by mass) are added to 100 grams of the SEBS solution, followed by addition of 20 grams of phase B.

The mass fractions of each of the phases and of the constituents are summarized below:

$\phi_B$=0.167

$\phi_x$=0.30

$\phi_{PS}$=0.047

$\phi_{STA}$=0(absence of surface-treating agent).

After stirring for 15 minutes under low-shear conditions, a stable emulsion with a modal diameter of 25 µm is obtained.

This example confirms that, when the active chemical substance x has surfactant properties similar to those of the dispersing copolymer, this copolymer makes it possible, by itself, in combination with the particulate stabilizer, to promote the dispersion of phase B in phase A.

EXAMPLE 9

Preparation of an Elastomeric Film

The solvent a is evaporated, under atmospheric pressure and at room temperature, from an emulsion as defined in Examples 2 to 8; an elastomeric film containing, in the form of a stable dispersion, droplets of solvent b, loaded with active chemical substance x, with a diameter $\geq 10$ µm is thus obtained.

As emerges from the text hereinabove, the invention is in no way limited to its modes of implementation, preparation and use which have just been described in greater detail; on the contrary, it encompasses all the variants which may occur to a person skilled in the art, without departing from the scope or context of the present invention.

What is claimed is:

1. Stable emulsion of at least one chemical substance x in an elastomer solution, which can be used for the preparation of an elastomeric film, comprising (1) a phase A comprising an elastomer dissolved in an apolar or relatively nonpolar organic solvent a, in which is dispersed (2) a phase B comprising at least said chemical substance x dissolved or dispersed in a polar solvent b, which is immiscible with the phase A, and (3) at least one dispersing agent selected from the group consisting of block copolymers and grafted copolymers, wherein:

the droplets of dispersed phase B have a diameter $\geq 10$ µm, said emulsion comprises, for the stabilization of said dispersed phase B, besides at least one dispersing copolymer comprising polyA sequences which are compatible with phase A and polyB sequences which are compatible with phase B, at least one particulate stabilizer selected from the group consisting of solid organic compounds of between 30 nm and 10 µm in size and solid inorganic compounds of between 5 nm and 10 µm in size, whose surface is organophilic in nature, the mass fraction $\phi_B$ of dispersed phase (phase B) in the emulsion, expressed by:

$$\phi_B = \frac{m_B}{m_B + m_A + m_{elastomer}}$$

is between 0.01 and 0.2, with $m_B$=mass of phase B (solvent b+active chemical substance x)

$m_A$=mass of solvent a $m_{elastomer}$=mass of the elastomer dissolved in a;

the mass fraction of the block or grafted copolymer, $\phi_{DC}$, expressed relative to the dispersed phase B:

$$\phi_{DC} = \frac{m_{DC}}{m_{DC} + m_B}$$

is between 0.001 and 0.3, with $m_B$=mass of phase B $m_{DC}$=mass of dispersing copolymer; and the mass fraction of particulate stabilizer (PS) $\phi_{PS}$, formed in situ or added as an adjuvant, expressed relative to the dispersed phase B:

$$\phi_{PS} = \frac{m_{PS}}{m_{PS} + m_B}$$

is between 0.001 and 0.5, with $m_{PS}$=mass of particulate stabilizer $m_B$=mass of phase B.

2. Emulsion according to claim 1, wherein said mass fraction of the block or grafted copolymer, $\phi_{DC}$, is between 0.001 and 0.2.

3. The stable emulsion claimed in claim 2, wherein the mass fraction of the block or grafted copolymer, $\phi_{DC}$, is between 0.01 and 0.1.

4. Emulsion according to claim 1, wherein when said particulate stabilizer is of organic nature, it is selected from the group consisting of organophilic block copolymers, organophilic grafted copolymers, identical to or different than those used as dispersing copolymers, which are capable of forming structures with a diameter of greater than 30 nm, and cellulose derivatives comprising, at their surface, a surface-treating agent capable of making said particulate stabilizer organophilic, the mass fraction of the surface-treating agent used to make the surface of the particles organophilic, i.e. $\phi_{STA}$, expressed relative to the particulate stabilizer:

$$\phi_{STA} = \frac{m_{STA}}{m_{PS} + m_{STA}}$$

being between 0.001 and 0.5, with $m_{STA}$=mass of the surface-treating agent $m_{PS}$=mass of particulate stabilizer.

5. Emulsion according to claim 4, characterized in that said mass fraction of the surface-treating agent, $\phi_{STA}$, is between 0.001 and 0.1.

6. The emulsion claimed in claim 4, wherein the cellulose derivative is microcellulose, starch, or certain finely divided polymers, comprising at their surface, a surface-treating agent capable of making said particulate stabilizer organophilic.

7. Emulsion according to claim 4, wherein said organophilic block or grafted copolymers are selected from the group consisting of copolymers containing a crystallizable polyB sequence and copolymers containing a crystallizable polyA sequence, which are soluble in phase A of the emulsion.

8. The emulsion claimed in claim 7, wherein the crystallizable polyB sequence is polyoxyethylene, polyethylene, polyamide, or polyester.

9. The emulsion claimed in claim 8, wherein the polyester is poly(caprolactone).

10. Emulsion according to claim 4, wherein the surface-treating agent is selected from the group consisting of block copolymers and grafted copolymers containing at least one polyA' sequence which is soluble in the solvent a, and a polyB' sequence capable of being adsorbed onto or binding to the surface of the particulate stabilizer, said polyA' and polyB' sequences being identical to or different than the polyA and polyB sequences and functionalized oligomers corresponding to the formula polyA'-F, in which F is a chemical function capable of being adsorbed onto the particulate stabilizer.

11. Emulsion according to claim 10, wherein F is a chemical function selected from the group consisting of acid, amine, alcohol functions and groups capable of reacting chemically with the surface of the particulate stabilizer.

12. The emulsion claimed in claim 11, wherein the group capable of reacting chemically with the surface of the particulate stabilizer is an epoxy, isocyanate or aziridine.

13. Emulsion according to claim 10, wherein the polyA' sequences are chosen from polymers which are soluble in the apolar or relatively nonpolar solvent a, which are miscible with a solution of elastomer in a solvent a, and the polyB' sequences are chosen from polymers capable of being adsorbed onto the surface of the particulate stabilizer.

14. Emulsion according to claim 13, wherein the proportions of polyA' sequence, expressed by mass relative to the sum of the polyA'+polyB' sequences, are between 10 and 90%, and the proportions of polyB' sequences are between 90 and 10%.

15. Emulsion according to claim 13 or claim 14, characterized in that the molar masses of the polyA' and polyB' sequences are between 150 and 200,000 daltons.

16. The emulsion as claimed in claim 13, wherein the polyA' sequence is selected from the group consisting of polydienes, polyolefins, polyethers, and silicones, and which is miscible with a solution of elastomer in a solvent a.

17. The emulsion claimed in claim 13, wherein the polyA' sequence is selected from the group consisting of polyisoprene, polybutadiene, polyisobutene, hydrogenated polybutadiene, hydrogenated polyisoprene, poly(4-tert-butylstyrene), polyoxypropylene, polyoxybutylene, polydimethyl-siloxane, poly(2-ethylhexyl methacrylate) and poly(lauryl methacrylate).

18. The emulsion claimed in claim 13, wherein the polyB' sequence is selected from the group consisting of polyoxyethylene, polyvinyl pyrrolidone, polyacrylic acid, poly(vinyl alcohol), quaternized poly(polyvinylpyrridine) and non-quaternized poly(vinylpyrridine).

19. The emulsion as claimed in claim 14, wherein the proportions of polyA' sequence, expressed by mass relative to the sum of the polyA'+polyB' sequences, are between 20 and 80%.

20. Emulsion according to claim 1, wherein when the particulate stabilizer is of inorganic type, this stabilizer is chosen from the group consisting of clays, silicas, talc, kaolin and derivatives of these products and comprising, at their surface, a surface-treating agent capable of making said particulate stabilizer organophilic, the mass fraction of the surface-treating agent used to make the surface of the particles organophilic, i.e. $\phi_{STA}$, expressed relative to the particulate stabilizer:

$$\phi_{STA} = \frac{m_{STA}}{m_{PS} + m_{STA}}$$

is between 0.001 and 0.5,
with $m_{STA}$=mass of the surface-treating agent
$m_{PS}$=mass of particulate stabilizer.

21. Emulsion according to claim 20, characterized in that said mass fraction of the surface treating agent, $\phi_{STA}$, is between 0.001 and 0.1.

22. Emulsion according to claim 1, wherein the dispersing block copolymer is a diblock copolymer of formula polyA-block-polyB, triblock copolymer of formula polyB-block-polyA-block-polyB (BAB), polyA-block-polyB-block-polyA (ABA), polyA-block-polyB-block-polyC (ABC), polyA-block-polyC-block-polyB (ACB), or a multiblock compound containing polyA, polyB and polyC sequences and the grafted dispersing copolymer is a compound of formula polyA-grafted-polyB, polyB-grafted-polyA, polyA-grafted-polyB, polyC, polyC-grafted-polyA, or polyB.

23. Emulsion according to claim 22, characterized in that the proportions of polyA sequence, expressed by mass relative to the sum of the polyA+polyB sequences, are between 10 and 90%, and the proportions of polyB sequences are between 90 and 10%, and the mass proportions of polyC sequences are between 0 and 50% relative to all of the sequences.

24. Emulsion according to claim 22, characterized in that the molar masses of the polyA, polyB and polyC sequences are between 1000 and 500,000 daltons.

25. Emulsion according to claim 1, wherein the polyA sequences, which are compatible with the solvent a, are selected from the group consisting of polydienes, polyolefins, polyethers and silicones, which are miscible with a solution of elastomer in a solvent a, the polyB sequences, which are compatible with the solvent b, are selected from the group consisting of polyoxyethylene, polyvinylpyrrolidone, polyacrylic acids, poly(vinyl alcohol) and quaternized poly(vinylpyridine), and the polyC sequences, which are either compatible with the solvent a or with the solvent b, or incompatible with the solvents a and b, are selected from the group consisting of acrylic and vinyl polymers.

26. The emulsion claimed in claim 25, wherein the polyA sequences are selected from the group consisting of polyisoprene, polybutadiene, polyisobutene, hydrogenated polybutadiene, hydrogenated polyisoprene, poly(4-tert-butylstyrene), polyoxypropylene, polyoxybutylene, polydimethylsiloxane, poly(2-ethylhexyl methacrylate) and poly(lauryl methacrylate).

27. The emulsion claimed in claim 25, wherein the polyC sequences are selected from the group consisting of poly (methyl methacrylate) and polystyrene.

28. Emulsion according to claim 1, wherein the elastomer is selected from the group consisting of polybutadiene, polyisoprene, polychloroprene, SBR (styrene butadiene rubber) copolymers, NBR (nitrile butadiene rubber) copolymers, SBS (styrene butadiene styrene) copolymers, SIS (styrene isoprene styrene) copolymers, SEBS (styrene ethylene-co-butylene styrene) copolymers, a mixture of said elastomers with one or more plasticizers, and a mixture of said elastomers with one or more flexibilizing agents.

29. Emulsion according to claim 1 wherein the solvent a is an aliphatic, aromatic or alicyclic hydrocarbon.

30. The emulsion claimed in claim 29, wherein the solvent a is methylcyclohexane, toluene, heptane, or mixtures of said solvents.

31. Emulsion according to claim 1, wherein the active chemical substance x is a compound capable of bringing about virtually instantaneous denaturing of proteins by means of simple contact.

32. Emulsion according to claim 31, wherein said active chemical substance x is a biocide.

33. Emulsion according to claim 31, wherein said biocide is a quaternary ammonium, biguanide, phthalaldehyde, phenolic derivative, benzylic derivative, formaldehyde, nonionic surfactant comprising at least one polyoxyethylene sequence, hexamidine, iodine-containing polyvinylpyrrolidone compound, nonionic surfactant with virucide activity, sodium and potassium dichromates and, hypochlorites, or a mixture of said biocides.

34. The emulsion as claimed in claim 33, wherein the quaternary ammonium is dimethyl didecylammonium chloride.

35. Emulsion according to claim 1, wherein the mass fraction of active chemical substance x, i.e. $\phi_x$, is expressed by $$\phi_x = \frac{m_x}{m_x + m_b} = \frac{m_x}{m_B}$$

and is between 0.01 and 0.7
with $m_x$=mass of active chemical substance x
$m_b$=mass of solvent b
$m_B$=mass of dispersed phase B.

36. The emulsion as claimed in claim 35, wherein the mass fraction of active chemical substance x, $\phi_x$, is between 0.1 and 0.4.

37. Emulsion according to claim 1, wherein the solvent b is immiscible with the solvent a and is a polyol or any other compound which is immiscible with the solvent a.

38. The emulsion claimed in claim 37, wherein the solvent b is a glycerol, ethylene glycol, or polyethylene glycol which is liquid at room temperature and has a molar mass of between 62 (ethylene glycol) and 750 daltons (PEG-750).

39. The emulsion claimed in claim 37, wherein the compound immiscible with solvent a is water, dimethyl sulfoxide, formamide, ethanolamine or mixtures of said compounds.

40. Emulsion according to claim 1, characterized in that it comprises several particulate stabilizers.

41. The stable emulsion claimed in claim 1, wherein the mass fraction of the block or grafted copolymer, $\phi_{DC}$, expressed relative to the dispersed phase B:

$$\phi_{DC} = \frac{m_{DC}}{m_{DC} + m_B}$$

is between 0.01 and 0.2.

42. The emulsion according to claim 1, wherein the active chemical substance x is a compound capable of bringing about virtually instantaneous denaturing of proteins by means of chemical reaction.

43. The emulsion according to claim 1, wherein the active chemical substance x is a compound capable of bringing about virtually instantaneous denaturing of proteins by means of a physicochemical effect.

44. The emulsion claimed in claim 43, wherein the means of physicochemical effect is modification of the surface tension.

45. Process for preparing a stable emulsion according to claim 1, wherein the particulate stabilizer is added during, or after formation of the emulsion, and further comprising the preparation of a phase A by dissolving the elastomer in an organic solvent a (phase A: solution of elastomer in organic solvent a), the preparation of a phase B, by mixing the active chemical substance x in an organic solvent b which is immiscible with phase A (phase B: solution or dispersion of active substance in an organic solvent b which is immiscible with phase A), the addition, to phase A or phase B, in proportions as defined above, of a block or grafted copolymer which serves essentially as dispersion copolymer, and the dispersion of phase A in phase B to obtain an emulsion in which phase A constitutes the dispersed phase, and the simultaneous or non-simultaneous addition, with stirring, of the particulate stabilizer which is organophilic or which has been made organophilic.

46. Elastomeric film, characterized in that it is obtained by evaporating the solvent a from an emulsion according to any one of claim 1.

47. A process for coating supports comprising applying the elastomeric film of claim 16 to a support.

48. Glove, characterized in that it comprises an elastomeric film according to claim 16.

49. Fingerstall, characterized in that it comprises an elastomeric film according to claim 16.

50. Condom, characterized in that it comprises an elastomeric film according to claim 16.

51. Dressing, characterized in that it comprises an elastomeric film according to claim 16.

52. Process for preparing an elastomeric film, characterized in that it comprises:

(a) the preparation of an emulsion according to claim 1, and (b) the evaporation of the organic solvent a to obtain an elastomeric film containing, in the form of a stable dispersion, droplets of solvent b, loaded with active chemical substance.

53. Stable emulsion of at least one chemical substance x in an elastomer solution, which can be used to prepare an elastomeric film, comprising (1) a phase A comprising an elastomer dissolved in an apolar or relatively nonpolar organic solvent a, in which is dispersed (2) a phase B comprising at least said chemical substance x, dissolved or dispersed in a polar solvent b, which is immiscible with the phase A, wherein:

the droplets of dispersed phase B have a diameter $\geq 10$ μm, said emulsion comprises, to stabilize said dispersed phase B, (1) at least one chemical substance x, this substance having surfactant properties and acting as a dispersant, said chemical substance x being selected from the group consisting of quaternary ammoniums, nonionic surfactants comprising at least one polyoxyethylene sequence and nonionic surfactants with virucide activity, and (2) at least one particulate stabilizer as defined in claim 1, the mass fraction $\phi_B$ of dispersed phase (phase B) in the emulsion, expressed by:

$$\phi_B = \frac{m_B}{m_B + m_A + m_{elastomer}}$$

is between 0.01 and 0.2,
with $m_B$=mass of phase B (solvent b+active chemical substance x)
$m_A$=mass of solvent a
$m_{elastomer}$=mass of the elastomer dissolved in a;
the mass fraction of the active chemical substance x, i.e. $\phi_x$, expressed by:

$$\phi_x = \frac{m_x}{m_x + m_b} = \frac{m_x}{m_B}$$

is between 0.01 and 0.7,
with $m_x$=mass of active chemical substance x
$m_b$=mass of solvent b
$m_B$=mass of dispersed phase B, and
the mass fraction of particulate stabilizer (PS), $\phi_{PS}$, formed in situ or added as an adjuvant, expressed relative to the dispersed phase B:

$$\phi_{PS} = \frac{m_{PS}}{m_{PS} + m_B}$$

is between 0.001 and 0.5,
with $m_{PS}$=mass of particulate stabilizer
$m_B$=mass of phase B.

54. Emulsion according to claim 53, characterized in that said elastomer, said solvent a, said solvent b and said particulate stabilizer are as defined in above.

55. Process for preparing a stable emulsion according to claim 53, wherein the particulate stabilizer is added before formation of the emulsion, and further comprising
the preparation of a phase A by dissolving the elastomer in an organic solvent a (phase A: solution of elastomer in the organic solvent a),
preparation of a phase B, by mixing the active chemical substance x, as defined in claim 53, in an organic solvent b which is immiscible with phase A (phase B: solution or dispersion of active substance in an organic solvent b which is immiscible with phase A),
the addition to phase A or phase B, in proportions as defined above, of an organophilic particulate stabilizer or one which has been made organophilic,
the dispersion of phase B in phase A to obtain an emulsion in which phase A constitutes the continuous phase and phase B constitutes the dispersed phase.

56. The process for preparing a stable emulsion claimed in claim 55, wherein the organophilic particulate stabilizer is formed from a block or grafted copolymer.

57. Process for preparing a stable emulsion according to claim 53, wherein the particulate stabilizer is added during or after formation of the emulsion, and further comprising:
the preparation of a phase A by dissolving the elastomer in an organic solvent a (phase A: solution of elastomer in the organic solvent a),
the preparation of a phase B, by mixing the active chemical substance x, as defined in claim 53, in an organic solvent b which is immiscible with phase A (phase B: solution or dispersion of active substance in an organic solvent b which is immiscible with phase A),
the dispersion of phase B into phase A to obtain an emulsion in which phase A constitutes the dispersed phase and phase B constitutes the dispersed phase, and the simultaneous or non-simultaneous addition, with stirring, of the particulate stabilizer which is organophilic or which has been made organophilic.

58. The process for preparing a stable emulsion claimed in claim 57, wherein the organophilic particulate stabilizer is formed from a block or grafted copolymer.

59. The stable emulsion claimed in claim 53, wherein the particulate stabilizer is a compound selected from the group consisting of block copolymers and grafted copolymers.

60. The stable emulsion claimed in claim 53, wherein the mass fraction of the chemical substance x, $\phi_x$, is between 0.1 and 0.4.

61. Process for preparing a stable emulsion according to claim 53, wherein the particulate stabilizer is added before formation of the emulsion, and further comprising
the preparation of a phase A by dissolving the elastomer in an organic solvent a (phase A: solution of elastomer in the organic solvent a),
preparation of a phase B, by mixing the active chemical substance x in an organic solvent b which is immiscible with phase A (phase B: solution or dispersion of active substance in an organic solvent b which is immiscible with phase A),
the addition to phase A or phase B, in proportions as defined above, of a block or grafted copolymer serving essentially as a dispersing copolymer; and an organophilic particulate stabilizer or one which is made organophilic,
the dispersion of phase B in phase A to obtain an emulsion in which phase A constitutes the continuous phase and phase B constitutes the dispersed phase.

* * * * *